United States Patent
Kolter et al.

(10) Patent No.: US 10,406,105 B2
(45) Date of Patent: *Sep. 10, 2019

(54) PHARMACEUTICAL FORMULATION FOR THE PRODUCTION OF RAPIDLY DISINTEGRATING TABLETS

(75) Inventors: Karl Kolter, Limburgerhof (DE); Michael Schönherr, Frankenthal (DE); Silke Gebert, Grünstadt (DE); Kathrin Meyer-Böhm, Feucht (DE); Angelika Maschke, Regensburg (DE)

(73) Assignee: BASF SE, Ludwigshafen (DE)

( * ) Notice: Subject to any disclaimer, the term of this patent is extended or adjusted under 35 U.S.C. 154(b) by 1848 days.

This patent is subject to a terminal disclaimer.

(21) Appl. No.: 12/663,046

(22) PCT Filed: Jun. 3, 2008

(86) PCT No.: PCT/EP2008/056805

§ 371 (c)(1),
(2), (4) Date: Dec. 4, 2009

(87) PCT Pub. No.: WO2008/148742

PCT Pub. Date: Dec. 11, 2008

(65) Prior Publication Data

US 2010/0178349 A1    Jul. 15, 2010

(30) Foreign Application Priority Data

Jun. 6, 2007 (EP) .................................. 07109722

(51) Int. Cl.
  *A61K 9/16* (2006.01)
  *A61K 9/20* (2006.01)
  *A61K 9/00* (2006.01)

(52) U.S. Cl.
  CPC .......... *A61K 9/2018* (2013.01); *A61K 9/0056* (2013.01); *A61K 9/2027* (2013.01); *A61K 9/2054* (2013.01)

(58) Field of Classification Search
  CPC ...... A61K 9/0056; A61K 9/2077; A61K 9/20; A61K 9/2018; A61K 9/2054; A61K 9/2027; A61K 9/2004
  USPC ....................................................... 424/489
  See application file for complete search history.

(56) References Cited

U.S. PATENT DOCUMENTS

| | | | |
|---|---|---|---|
| 4,658,002 A | 4/1987 | Tschang et al. | |
| 4,871,549 A | 10/1989 | Ueda et al. | |
| 5,569,469 A | 10/1996 | Lovrecich | |
| 5,874,418 A | 2/1999 | Stella et al. | |
| 6,066,334 A * | 5/2000 | Kolter et al. | 424/465 |
| 6,187,339 B1 | 2/2001 | de Haan et al. | |
| 6,274,727 B1 | 8/2001 | Maui et al. | |
| 6,329,334 B1 | 12/2001 | Bertleff et al. | |
| 6,495,177 B1 | 12/2002 | deVries et al. | |
| 6,677,417 B2 | 1/2004 | Meffert et al. | |
| 6,696,085 B2 | 2/2004 | Rault et al. | |
| 6,723,348 B2 | 4/2004 | Faham et al. | |
| 2001/0010825 A1 | 8/2001 | Shimizu et al. | |
| 2001/0016728 A1 | 8/2001 | Kelley | |
| 2002/0071864 A1 | 6/2002 | Kim et al. | |
| 2002/0127277 A1 | 9/2002 | Qiu et al. | |
| 2002/0147232 A1* | 10/2002 | Sundgreen et al. | 514/474 |
| 2002/0168404 A1 | 11/2002 | Rault et al. | |
| 2004/0058896 A1 | 3/2004 | Dietrich et al. | |
| 2004/0110661 A1 | 6/2004 | Dietrich et al. | |
| 2005/0163835 A1* | 7/2005 | Gellert | A61K 9/284 424/464 |
| 2005/0169986 A1* | 8/2005 | Tian et al. | 424/464 |
| 2005/0244343 A1 | 11/2005 | Witham et al. | |
| 2005/0244492 A1 | 11/2005 | Mehra et al. | |
| 2005/0287177 A1 | 12/2005 | Goodson et al. | |
| 2006/0115524 A1* | 6/2006 | Eliasen | 424/451 |
| 2008/0299191 A1* | 12/2008 | Kolter | A61K 9/0056 424/464 |
| 2008/0299194 A1 | 12/2008 | Kolter et al. | |
| 2010/0173859 A1 | 7/2010 | Kolter et al. | |
| 2010/0178306 A1 | 7/2010 | Kolter et al. | |
| 2010/0178349 A1 | 7/2010 | Kolter et al. | |
| 2010/0184785 A1 | 7/2010 | Kolter et al. | |

FOREIGN PATENT DOCUMENTS

| | | |
|---|---|---|
| EP | 0177812 A1 | 4/1986 |
| EP | 0839526 A2 | 5/1998 |
| EP | 1036839 A2 | 9/2000 |
| JP | 2004026521 A | 1/2004 |

(Continued)

OTHER PUBLICATIONS

U.S. Appl. No. 12/663,036, filed Dec. 2009, Kolter et al.*
U.S. Appl. No. 12/538,236, filed Jun. 2008, Kolter et al.*
Technical Information—Insoluble Kollidon® grades, pp. 1-16, Sep. 2011.*
Excipients and Activities for Pharma, p. 1-16, published on Oct. 2006.*
Bühler, V. "Polyvinylpyrrolidone Excipients for Pharmaceuticals," Springer Verlag Berlin Heidelberg, pp. 128-131, 2005.
See BASF, Accelerators—Kollidon CL, Kollidon CL-F, Kollidon CL-SF, Kollidon CL-M at http://www.basf-chemtrade.de/images/stories/broschueren/PHI/basf_kollidon_grades.pdf—accessed Nov. 23, 2009.

Primary Examiner — Mina Haghighatian
Assistant Examiner — Mei Ping Chui
(74) Attorney, Agent, or Firm — Drinker Biddle & Reath LLP

(57) ABSTRACT

Pharmaceutical formulation in the form of agglomerates comprising
A) an excipient content composed of
  a) 60-97% by weight of sugar or sugar alcohols,
  b) 1-25% by weight of a disintegrant,
  c) 1-15% by weight of water-insoluble, film-forming polymers
  d) 0-15% by weight of water-soluble polymers and
  e) 0-15% by weight of further pharmaceutically customary excipients the total of the components a) to e) being 100% by weight,
and
B) at least one active ingredient.

17 Claims, No Drawings

(56) References Cited

FOREIGN PATENT DOCUMENTS

| | | |
|---|---|---|
| JP | 2004265216 A | 9/2004 |
| JP | 2006199632 A | 8/2006 |
| WO | WO-98/22094 A2 | 5/1998 |
| WO | WO-03/032978 A1 | 4/2003 |
| WO | WO-03/041683 A2 | 5/2003 |
| WO | WO-03/051338 A1 | 6/2003 |
| WO | WO-03/051388 A2 | 6/2003 |
| WO | WO-03/072084 A1 | 9/2003 |
| WO | WO-2005/105049 A2 | 11/2005 |
| WO | WO-2006/029787 A1 | 3/2006 |
| WO | WO-2007/071580 A1 | 6/2007 |
| WO | WO-2007/071581 A2 | 6/2007 |
| WO | WO-2008/148731 A1 | 12/2008 |
| WO | WO-2008/148733 A2 | 12/2008 |
| WO | WO-2008/148734 A1 | 12/2008 |
| WO | WO-2008/148742 A2 | 12/2008 |

\* cited by examiner

PHARMACEUTICAL FORMULATION FOR THE PRODUCTION OF RAPIDLY DISINTEGRATING TABLETS

RELATED APPLICATIONS

This application is a national stage application (under 35 U.S.C. § 371) of PCT/EP2008/056805, filed Jun. 3, 2008, which claims benefit of European Application No. 07109722.4, filed Jun. 6, 2007.

The present invention relates to pharmaceutical formulations in the form of agglomerates for the production of rapidly disintegrating tablets, comprising sugar or sugar alcohols, disintegrant and water-insoluble polymers besides at least one active ingredient.

Tablets which disintegrate rapidly in the mouth and/or dissolve rapidly are becoming increasingly important for the oral administration of medicaments. Such tablets must disintegrate within a short time, preferably within 30 seconds, in the oral cavity and have a pleasant taste and must not leave behind a gritty sensation. Furthermore they should be easy to produce, with direct tabletting having considerable advantages over wet granulation, and should have high mechanical strength so that they withstand packaging procedures, transport and also pressing out from packaging without damage.

The products and processes described to date do not meet these requirements or do so only very inadequately.

Rapidly disintegrating tablets frequently consist of sugar and sugar alcohols, effervescent systems, microcrystalline cellulose and other water-insoluble fillers, calcium hydrogen phosphate, cellulose derivatives, cornstarch or polypeptides. Furthermore, water-soluble polymers, conventional disintegrants (crosslinked PVP, sodium and calcium salts of crosslinked carboxymethylcellulose, the sodium salt of carboxymethyl starch, low-substituted hydroxypropylcellulose L-HPC) and substantially inorganic water-insoluble constituents (silicas, silicates, inorganic pigments) are used. Furthermore, the tablets may also comprise surfactants.

WO 2003/051338 describes a directly tablettable and readily compressible excipient formulation which comprises mannitol and sorbitol. First, an excipient premix is prepared by dissolution of mannitol and sorbitol in water and subsequent spray drying (customary spray drying and SBD method). Mannitol may also be added to this coprocessed mixture. Tablets which additionally comprise disintegrant, glidant, pigment and an active ingredient are said to disintegrate within 60 seconds in the oral cavity.

US 2002/0071864 A1 describes a tablet which disintegrates within 60 seconds in the oral cavity and is mainly formulated from a physical mixture of spray-dried mannitol and a coarse-particle crosslinked polyvinylpyrrolidone and a limited selection of active ingredients. These tablets have a hardness of about 40 N and produce an unpleasant, gritty mouthfeel.

According to U.S. Pat. No. 6,696,085 B2 a methacrylic acid copolymer of type C is to be used as a disintegrant. The methacrylic acid copolymer of type C is a polymer which is resistant to gastric fluid and insoluble in the acidic pH range but water-soluble in the pH range of 7 as is present in the oral cavity. In addition to low hardness (<20 N), the tablets have high friability (>7%) and have a high proportion in the region of 15% by weight of a coarse-particle disintegrant. They consequently have low mechanical strength and, owing to the high proportion of coarse-particle disintegrant, produce an unpleasant, gritty mouthfeel.

EP 0839526 A2 describes a pharmaceutical dosage form consisting of an active ingredient, erythritol, crystalline cellulose and a disintegrant. Furthermore, mannitol is incorporated and crosslinked polyvinylpyrrolidone is used as a disintegrant, so that a physical mixture forms. The tablets are said to decompose within 60 seconds in the oral cavity.

The application JP 2004-265216 describes a tablet which disintegrates in the mouth within 60 seconds and consists of an active ingredient, a water-soluble polyvinyl alcohol/polyethylene glycol copolymer, sugar/sugar alcohol (mannitol) and disintegrant.

It was an object of the present invention to provide tablets which disintegrate rapidly in the mouth, leave behind a pleasant mouthfeel, are mechanically very stable and exhibit high content uniformity.

Accordingly, a pharmaceutical preparation for the production of tablets which disintegrate rapidly in the mouth was found, which consists of agglomerates comprising
  A) a content of excipients composed of
    a) 60-97% by weight of at least one sugar or sugar alcohol or mixtures thereof,
    b) 1-25% by weight of a disintegrant,
    c) 1-15% by weight of water-insoluble polymers,
    d) 0-15% by weight of water-soluble polymers, and
    e) 0-15% by weight of further pharmaceutically customary excipients, the total of the components a) to e) being 100% by weight,
and
  B) at least one active ingredient.

Furthermore, processes for the production of such agglomerates have been found.

Furthermore, tablets which disintegrate rapidly in the mouth and comprise such preparations were found. The tablets disintegrate in the mouth or in an aqueous medium within 60 seconds, preferably within 30 seconds, particularly preferably within 20 seconds. "The tablets exhibit a disintegration time of <60 seconds in phosphate buffer, pH 7.2, at 37° C. The disintegration time is determined in a disintegration tester complying with USP or Pharm. Eur."

The excipient content A) has the following specific composition:

The pharmaceutical preparations comprise, as component a), from 60 to 97% by weight, preferably from 70 to 95% by weight, particularly preferably from 75 to 93% by weight, of a sugar, sugar alcohol or mixtures thereof. Suitable sugars or sugar alcohols are trehalose, mannitol, erythritol, isomalt, maltitol, lactitol, xylitol and sorbitol. The sugar or sugar alcohol components are preferably finely divided, with average particle sizes of from 5 to 100 μm. If desired, the particle sizes can be adjusted by grinding. Preferred particle sizes are from 30 to 50 μm. However, it may also be advisable to use particle sizes smaller than 30 μm. It may likewise be advisable to employ sugars or sugar alcohols which comprise mixtures of fractions differing in particle size, for example mixtures of 30 to 70% by weight of a particle size fraction having an average particle size of <30 μm and 30 to 70% by weight of a particle size fraction having an average particle size of 30 to 50 μm. Mannitol, erythritol or mixtures thereof are preferably employed.

Disintegrants in amounts of from 1 to 25% by weight, preferably 2 to 15% by weight, particularly preferably 3 to 10% by weight, are employed as component b). The disintegrants are preferably selected from the group consisting of crosslinked polyvinyl-pyrrolidones, croscarmellose, sodium carboxymethylstarch and L-hydroxypropyl-cellulose. Croscarmellose means according to the invention the sodium and/or calcium salts of crosslinked carboxymethylcellulose. Preferred L-hydroxypropylcelluloses have 5 to 16% hydroxypropoxy groups.

Crosslinked polyvinylpyrrolidones are particularly preferred. Such crosslinked polyvinyl-pyrrolidones are water-insoluble but non film-forming. The crosslinked polyvinylpyrrolidone may have an average particle size of from 2 to 60 µm, preferably less than 50 µm, particularly preferably less than 30 µm. Crosslinked polyvinyl-pyrrolidones having a hydration capacity of greater than 6.5 g/g are very particularly preferred. In this connection, the hydration capacity is determined by the following method: 2 g of polymer are weighed into a centrifuge tube and allowed to swell with 40 ml of water for 15 minutes. Thereafter, centrifuging is effected for 15 minutes at 2000 rpm and the supernatant liquid is poured off as completely as possible.

Hydration capacity=Final weight−tare Initial weight

In the formulation, the high hydration capacity of the crosslinked polyvinylpyrrolidone leads to a very rapid disintegration and gives a particularly soft mouthfeel.

Water-insoluble polymers in amounts of from 1 to 15% by weight, preferably from 1 to 10% by weight, are used as component c). These are polymers. Preferred polymers are those which are insoluble in the pH range from 1 to 14, i.e. have a water insolubility which is pH independent at every pH. However, polymers which are water-insoluble at any pH in the pH range from 6 to 14 are also suitable.

The polymers should be film-forming polymers. In this context, film-forming means that the polymers have a minimum film forming temperature of from −20 to +150° C., preferably from 0 to 100° C., in aqueous dispersion.

Suitable polymers are polyvinyl acetate, ethylcellulose, methyl methacrylate/ethyl acrylate copolymers, ethyl acrylate/methyl methacrylate/trimethylammoniumethyl methacrylate terpolymers. Butyl methacrylate/methyl methacrylate/dimethylaminoethyl methacrylate terpolymers.

The acrylate/methacrylate copolymers are described in more detail in the European Pharmacopoeia as Polyacrylate Dispersion 30%, in the USP as Ammonia Methacrylate Copolymer and in JPE as Aminoalkyl Methacrylate Copolymer E. Polyvinyl acetate is used as preferred component c). This may be used as an aqueous dispersion having solids contents of from 10 to 45% by weight. In addition, a preferred polyvinyl acetate is one having a molecular weight of from 100 000 to 1 000 000 daltons, particularly preferably from 200 000 to 800 000 daltons.

Furthermore, the formulations may comprise water-soluble polymers in amounts of from 0 to 15% by weight as component d). Suitable water-soluble polymers are, for example, polyvinylpyrrolidones, vinylpyrrolidone/vinyl acetate copolymers, polyvinyl alcohols, polyvinyl alcohol/polyethylene glycol graft copolymers, polyethylene glycols, ethylene glycol/propylene glycol block copolymers, hydroxypropylmethylcellulose, hydroxypropylcellulose, hydroxyethylcellulose, carrageenans, pectins, xanthans and alginates.

If desired, taste and appearance of the tablets obtained from the formulations can be further improved by adding pharmaceutically customary excipients (components e)) in amounts of from 0 to 15% by weight, for example such as acidifiers, buffer substances, sweeteners, flavors, flavor enhancers and colorants. The following substances are particularly suitable here: citric acid, tartaric acid, ascorbic acid, sodium dihydrogen phosphate, cyclamate, saccharin sodium, aspartame, menthol, peppermint flavor, fruit flavors, vanilla flavor, glutamate, riboflavin, beta-carotene, water-soluble colorants and finely divided color lakes.

By adding thickeners, such as high molecular weight polysaccharides, the mouthfeel can be additionally improved by increasing the softness and the sensation of volume.

Furthermore, surfactants may also be added as components e). Suitable surfactants are, for example, sodium laurylsulfate, dioctyl sulfosuccinate, alkoxylated sorbitan esters, such as polysorbate 80, polyalkoxylated derivatives of castor oil or hydrogenated castor oil, for example Cremophor® RH 40, alkoxylated fatty acids, alkoxylated hydroxyl fatty acids, alkoxylated fatty alcohols, alkali metal salts of fatty acids and lecithins.

Furthermore, finely divided pigments may also be added for further improvement of the disintegration, because they increase the internal interfaces and hence water can penetrate more rapidly into the tablet. These pigments, such as iron oxides, titanium dioxide, colloidal or precipitated silica, calcium carbonates or calcium phosphates, must of course be very finely divided since otherwise a grainy taste once again results.

It is possible to employ as active ingredients B) in principle all active ingredients. The active ingredients mentioned below are preferably employed, particularly preferably in the stated dosages.

Zolmitriptan 2.5 mg, rizatriptan 5 mg, diphenhydramin-HCl (taste-masked) 20 mg, brompheniramine 5 mg, chlorpheniramine 5 mg, pseudoephedrine (taste-masked) 30 mg, paracetamol (taste-masked) 250 mg, ibuprofen (taste-masked) 200 mg, acetylsalicylic acid 250 mg (taste-masked), hyoscyamine sulfate 0.125 mg, mirtazapine 15 mg, selegeline HCl 1.25 mg, ondansetron 4 mg, olanzapine 5 mg, clonazepam 1 mg, cetirizine hydrochloride 10 mg, desloratadine 5 mg, enalapril maleate 5 mg, domperidone maleate 10 mg, scopolamine 0.25 mg, oxazepam 15 mg, lorazepam 2.5 mg, clozapine 25 mg, dihydroergotamine mesylate 5 mg, nicergoline 5 mg, phloroglucinol 80 mg, metopimazine 7.5 mg, triazolam 0.5 mg, protizolam 0.5 mg, tramadol 50 mg, zolpidem tartrate 5 mg, cisapride 5 mg, risperidone 2 mg, azithromycin 100 mg (taste-masked), roxithromycin 50 mg (taste-masked), clarithromycin 125 mg (taste-masked), erythromycin estolate 250 mg (taste-masked), apomorphine 20 mg, fentanyl 0.6 mg.

Mixtures of active ingredients can also be employed. Particularly suitable mixtures are: paracetamol or ibuprofen or acetylsalicylic acid and pseudoephedrine, paracetamol or ibuprofen or acetylsalicylic acid and diphenhydramine or chlorpheniramine or brompheniramine or loratadine.

The stated dosages represent the absolute amounts of the respective active ingredient per pharmaceutical form. The concentration of the excipient content and of the active ingredient content in the finished pharmaceutical form depends on the size of the pharmaceutical form. In the case of tablets, usual tablet weights of: 50 to 1000 mg, preferably 80 to 600 mg.

The active ingredients can also be provided with a conventional taste-masking coating. Suitable polymers for such coatings are: aminoalkylmethacrylate copolymer E (Eudragit E or EPO), polyvinyl alcohols in various formulations (Opadry AMB, Kollicoat Protect), combinations of water-insoluble polymers such as, for example, polyvinyl acetate, poly(meth)acrylates (Eudragit NE 30 D, NM 30D, RL, RS, RD, Kollicoat EMM 30 D), ethylcellulose with water-soluble or water-swellable low or high molecular weight substances (povidone, copovidone, HPMC, HPC, polyethylene glycols, poloxamers, polyethylene glycol-polyvinyl alcohol graft copolymers, sugars, sugar alcohols, organic or inorganic salts), combinations of water-soluble film formers (polyethylene glycol-polyvinyl alcohol graft copolymers, HPMC, polyvinyl alcohols) with fats, waxes, fatty acids and fatty alcohols.

The formulations according to the invention can be produced by agglomeration in mixers, fluidized-bed apparatuses or spray towers. Solid starting materials and granulating liquid are first mixed with one another and the moist mixed material is then dried. According to the present invention, the granulating liquid used is an aqueous dispersion of component c), of the water-insoluble polymer.

In one embodiment of the invention, one or more active ingredients are introduced first together with the sugar or sugar alcohol, disintegrant and, if desired, components d) and e) into the fluidized bed.

In fluidized-bed agglomeration, an aqueous dispersion of the water-insoluble polymer (component c)) is sprayed onto a fluidized mixture of sugar or sugar alcohol, disintegrant, active ingredients and, if appropriate, further components d) and e), resulting in the agglomeration of the fine particles. The inlet air temperatures are 30 to 100° C., and the outlet air temperatures are 20 to 70° C.

Especially with this agglomeration it is possible to incorporate as further components e) the following excipients: colorants, sweeteners, flavorings, further disintegrants, carbonates, bicarbonates, acidifiers or further excipients. The use of colorants, in which case it is possible to use inorganic pigments, organic color lakes or water-soluble colorants, leads for example to uniformly colored, rapidly disintegrating tablets. Examples of suitable colorants are riboflavin, beta-carotene, anthocyans, carmine, indigocarmine, orange yellow S, quinoline yellow, indigotine lake, brilliant blue, sunset yellow. These further substances can either be put in solid form into the fluidized bed initial charge or be dissolved or dispersed in the dispersion of components c). If the dispersion is incompatible with such a substance, the latter can also be sprayed on in solution or as suspension before or after the agglomeration with the dispersion of components c).

In production in spray towers, the so-called FSD or SBD technology (FSD: fluidized spray drying; SBD: spray bed drying) is preferably used. Here, a solution of the sugar or sugar alcohol in water is first spray-dried and the addition of disintegrants and the spraying in of an aqueous dispersion of the water-insoluble polymer are effected in the lower part of the spray dryer or in a connected fluidized bed, with the result that the particles agglomerate. In a special variant, the disintegrant is dispersed in the solution of the sugar or sugar alcohol in water, and the process is carried out as described above. Fine particles can furthermore be blown again in front of the spray nozzle of the sugar or sugar alcohol solution and additionally agglomerated. A procedure starting from the crystalline form of the sugar or sugar alcohol is also possible in the spray tower, FSD or SBD. The crystalline sugar or sugar alcohol is added at the top of the spray tower or in the recycle stream of fine material. By spraying an aqueous dispersion of the water-insoluble polymer, this crystalline solid is agglomerated in the tower.

It may prove advantageous for the agglomeration process to carry out a multistage spray process. At the beginning, the spray rate is kept low in order to prevent over-moistening of the initially charged product and hence adhesion thereof. With increasing duration of the process, the spray rate can be increased and thus the tendency to agglomerate can be raised. It is also possible to adapt the inlet air flow rate and/or temperature in an appropriate manner during the process. Particularly during the drying phase, it is advantageous to reduce the inlet air flow rate and hence to prevent abrasion of the agglomerates due to a high mechanical stress.

The fineness of the spray droplet of the binder solution or dispersion (adjustable via the atomization gas pressure), the nozzle geometry and the distance from the nozzle to the product bed may be regarded as further adaptation parameters for the agglomerate size. The finer and more uniform the spraying, the finer and more uniform are the resulting agglomerates. The further away the nozzle is from the product bed, the poorer is the agglomeration behavior.

Furthermore, the agglomeration can also take place in a mixer by continuous aggregation with mixing. Such a continuous form of aggregation with mixing is the so-called "Schugi granulation". There, solid starting materials and the granulating liquid comprising the water-insoluble polymer are thoroughly mixed with one another in a continuously operating vertically arranged high-speed mixer (cf. also M. Bohnet, "Mechanische Verfahrenstechnik", Wiley VCH Verlag, Weinheim 2004, page 198 et seq.).

According to a particular embodiment, the disintegrant is suspended in the aqueous dispersion of the water-insoluble polymer.

The agglomerates thus obtained have an average particle size of 100-600 μm, preferably 120-500 μm and particularly preferably 140-400 μm. The water-insoluble, film-forming polymer serves as an agglomerating agent for agglomerating the fine sugar or sugar alcohol crystals, the active ingredient particles and the disintegrant and, if appropriate, further excipients to larger particles.

In a further embodiment of the invention, it is also possible initially to agglomerate the excipient content A) and then for an agglomeration to take place in a further granulation step with one or more active ingredients.

In a variant of this embodiment, the agglomerated excipient content and active ingredient are initially introduced into the fluidized bed and granulated by means of a binder solution. The binder solution comprises as binder in this case a water-soluble polymer selected from the group of components d). It is preferably an aqueous solution. The binder concentration can be from 1 to 40% by weight.

Preferred binders are water-soluble polyvinylpyrrolidones having Fikentscher K values of from 12 to 120, in particular K30, vinylpyrrolidone-vinyl acetate copolymers composed of 30 to 70% by weight N-vinylpyrrolidone, preferably 40 to 60% by weight, and 30 to 70% by weight, preferably 40 to 60% by weight, vinyl acetate, also polyvinyl alcohols, graft copolymers of polyethylene glycol and polyvinyl alcohol, hydroxypropyl-methylcellulose, hydroxypropylcellulose, hydroxyethylcellulose, and gelatin.

In a second variant, the agglomerated excipient content is initially introduced into the fluidized bed, and the active ingredient content is incorporated into the binder solution described above.

In a further variant, in which the water-soluble binder (component d)) is obligatorily already present in the preagglomerated excipient content, preferably in amounts of from 0.2 to 10% by weight, the granulating liquid employed is water without polymeric binder. Other excipients from the group of component e) can in this case be added to the water used for the granulation. It may further be advisable to add one of said sugars or sugar alcohols to the water.

The apparatuses and process parameters used for all these variants of the embodiment in which the excipient content is initially agglomerated are otherwise the same as described above for the simultaneous agglomeration are excipient content and active ingredient content.

The formulations according to the invention can advantageously also be used for the production of tablets which are left to disintegrate in a glass of water prior to use. The production of tablets which are swallowed intact is of course also possible.

For the production of the tablets, the customary processes can be used, direct tabletting and roll compacting having particular advantages. Owing to the particular properties of the formulations according to the invention, as a rule only active ingredient, formulation according to the invention and a lubricant are required. The tablet formulation is therefore very simple and very reproducible and the process is easy to validate.

Surprisingly, it was found that a water-insoluble film-forming polymer considerably accelerates the disintegration of tablets. This is all the more surprising since such polymers are as a rule used for the preparation of slow-release pharmaceutical forms which do not disintegrate within several hours. The disintegration times with the use of polyvinyl acetate as the water-insoluble polymer are considerably shorter than in the case of water-soluble polymers.

Furthermore, the formulations according to the invention have extremely good flowabilities and compressibilities, which lead to mechanically very stable tablets. The hardness of the tablets produced with the aid of the pharmaceutical formulations according to the invention is >40 N. Frequently, the hardnesses are above 60 N, even with the use of active ingredients which are difficult to compress. The friabilities are <0.2%. There is therefore no damage during customary tablet handling.

Owing to the fine crosslinked polyvinylpyrrolidone, the tablets show virtually no changes in the tablet surface when stored under moist conditions. In contrast to coarse crosslinked polyvinylpyrrolidone, there is no pimple formation due to greatly swollen particles. The formulations according to the invention are therefore very stable during storage and retain their attractive appearance.

The active ingredient particles are firmly bound to the excipient particles through the granulation, and segregation is no longer possible. The content uniformity of tablets, especially of tablets with a low active ingredient content, is considerably improved thereby. The reproducibility of the tablet properties is considerably improved. It is possible in this way to process active ingredients with physicochemical properties which differ greatly by comparison with the excipients.

Surprisingly, the granulation together with active ingredients does not lead to a slowing of the rate of dissolution although this would be expected owing to the stronger adhesion of the particles.

The pharmaceutical preparations can also be used in other pharmaceutical forms: examples of further pharmaceutical forms are sachets or granule containers with metering device.

EXAMPLES

Production took place by a two-stage agglomeration process, initially choosing a lower spray rate and subsequently increasing the spray rate. The following production conditions were used in a two-stage agglomeration process:

| | |
|---|---|
| Batch size: | 0.6 kg |
| Concentration of the aqueous binder solution/dispersion: | 20% by weight |
| Inlet air temperature: | 50° C. |
| Outlet air temperature: | 30° C. |
| Initial spray rate (10 min): | 15 g/min |
| Spray rate after adjustment: | 20 g/min |

The disintegrant used was: Kollidon CL-SF, from BASF: crospovidone, crosslinked polyvinylpyrrolidone with an average particle size of 17 μm.

The polyvinyl acetate used was: Kollicoat SR 30 D, from BASF: commercially available aqueous polyvinyl acetate dispersion, stabilized with 2.7% by weight polyvinyl-pyrrolidone and 0.3% by weight sodium dodecylsulfate
Kollicoat® IR, from BASF: commercially available graft polymer composed of 75% by weight polyvinyl alcohol and 25% by weight polyethylene glycol, average Mw. 45 000 D
Kollidon® VA 64, from BASF: copovidone, copolymer composed of 60% by weight NVP and 40% by weight VAc

TABLE 1

Composition of agglomerates A to E in % by weight

| | A | B | C | D | E |
|---|---|---|---|---|---|
| Mannitol ($d_{0.5}$: 36 μm) | 89.32 | 73.0 | 83.2 | 86.6 | 89.32 |
| Kollidon ® CL-SF | 5.00 | 5.0 | 5.0 | 5.0 | 5.00 |
| Kollicoat ® SR 30 D (solid) | 5.00 | 5.0 | 5.0 | 5.0 | 5.00 |
| Loperamid HCl | 0.68 | — | — | — | — |
| Caffeine (fine powder) | — | 17.0 | — | — | — |
| Piroxicam | — | — | — | 3.4 | — |
| Famotidine | — | — | 6.8 | — | — |
| Risperidone | — | — | — | — | 0.68 |

The agglomerates produced in this way were mixed with 2.0% by weight lubricant (Mg stearate) in a Turbula mixer for 10 min. These mixtures were then compressed in a fully instrumented eccentric press (Korsch XP 1) to biplanar tablets with a weight of 300 mg, a diameter of 10 mm and a hardness of 40-55N.

The tablets were investigated for hardness (HT-TMB-Cl-12 F tablet tester from Kraemer), disintegration time in phosphate buffer of pH 7.2 (ZT 74 disintegration tester, Erweka) and release rate in simulated gastric fluid of pH 1.2 (release apparatus, Erweka).

TABLE 2

Tablet properties of formulations A to E

| | Tabletting data | Tablet parameters | | |
|---|---|---|---|---|
| | Compressive force [kN] | Hardness [N] | Disintegration time [s] | Release rate [% after 10 min] |
| A | 3.5 | 46 | 18 | 70 |
| B | 3.2 | 48 | 23 | 100 |
| C | 4.3 | 51 | 37 | 100 |
| D | 4.1 | 42 | 35 | 60 |
| E | 3.9 | 56 | 27 | 100 |

Granulation of the Preagglomerated Excipient Content with Active Ingredient

The rapidly disintegrating excipient was produced by fluidized bed agglomeration of mannitol (90% by weight) and crosslinked PVP (5% by weight) with polyvinyl acetate (5% by weight). The product produced in this way was subjected to a further granulation step, with in each case preagglomerated excipient and active ingredient being introduced first in the first experiment, and being granulated by means of a binder solution, and only preagglomerated excipient being introduced first in the second variant, the active ingredient being incorporated into the binder solution.

The granulation processes employed were both the fluidized bed process and mixer granulation. It is possible in principle to use all granulation processes. The binder can also be admixed dry and then water can be sprayed on or added.

In a special embodiment, the rapidly disintegrating excipient was granulated with the active ingredient only by adding water. It was possible in this case to improve the granulation effect by adding a sugar or sugar alcohol to the water.

In a similar way to that described for variant 1 it is also possible to use in this granulation colorants, sweeteners, flavors, further disintegrants, carbonates, bicarbonates, acidifiers or further excipients.

TABLE 3

Process parameters

| | Fluidized bed granulation | | Mixer granulation |
|---|---|---|---|
| | F | G | H/J |
| Batch size [g] | 600 | 600 | 1200 |
| Inlet air temperature [° C.] | 50 | 55 | — |
| Outlet air temperature [° C.] | 30 | 30 | — |
| Spray rate [g/min] | 17 | 20 | 30 |
| Mixer [Upm] | — | — | 200 |
| Chopper [Upm] | — | — | 400 |
| Granulation time [min] | — | — | 10 |
| Remarks | Granulation with binder solution | Active ingredient is incorporated into the binder solution | Active ingredient is incorporated into the binder solution (experiment J) |

TABLE 4

Composition of agglomerates F to J in % by weight

| | Fluidized bed granulation | | Mixer granulation | |
|---|---|---|---|---|
| | F | G | H | J |
| Mannitol ($d_{0.5}$: 36 μm) | 86.64 | 71.94 | 71.94 | 86.64 |
| Kollidon CL-SF | 4.81 | 4.00 | 4.00 | 4.81 |
| Kollicoat SR 30 D (solid) | 4.81 | 4.00 | 4.00 | 4.81 |
| Loperamid HCl | 0.68 | — | — | 0.68 |
| Caffeine (fine powder) | — | 17.00 | 17.00 | — |
| Kollidon 30 | — | — | — | 3.06 |
| Kollicoat ® IR | 3.06 | — | 3.06 | — |
| Kollidon ® VA 64 | — | 3.06 | — | — |

The granules resulting from the mixer granulation were sieved after the granulation through a 1 mm sieve, dried on a tray at room temperature overnight and then passed through a 0.8 mm sieve.

The agglomerates produced in this way were mixed with 2.0% by weight lubricant (Mg stearate) and, in examples F and J, also with additional 3% Kollidon CL-SF, and then compressed in a rotary tablet press (Korsch XL 100) to tablets having a hardness of 40-50N.

The tablets were investigated for hardness (HT-TMB-Cl-12 F tablet tester from Kraemer), disintegration time in phosphate buffer of pH 7.2 (ZT 74 disintegration tester, Erweka) and release rate in simulated gastric fluid of pH 1.2 (release apparatus, Erweka).

TABLE 5

Tablet properties of formulations F to J

| | Hardness [N] | Friability [%] | Disintegration time [s] | Release rate [% after 10 min] |
|---|---|---|---|---|
| F | 43 | <0.2 | 89 | 60 |
| G | 48 | <0.2 | 62 | 95 |
| H | 42 | <0.2 | 51 | 100 |
| J | 45 | <0.2 | 59 | 70 |

We claim:

1. A pharmaceutical formulation in the form of agglomerates comprising:
   A) an excipient content composed of:
      a) 60-97% by weight of sugar or sugar alcohols,
      b) 1-25% by weight of a disintegrant consisting of crospovidone with a hydration capacity of greater than 6.5 g/g,
      c) 1-15% by weight of water-insoluble, film-forming polymers,
      d) 0-15% by weight of water-soluble polymers, and
      e) 0-15% by weight of further pharmaceutically customary excipients, the total of the components a) to e) being 100% by weight,
      and
   B) at least one pharmaceutically active ingredient,
   wherein the crospovidone with a hydration capacity of greater than 6.5 g/g has an average particle size of 17 μm to 30 μm.

2. The formulation according to claim 1, where the average particle size of the agglomerates is from 100 μm to 600 μm.

3. The formulation according to claim 1, wherein the sugar or sugar alcohol (a) is mannitol or erythritol, or mixtures thereof.

4. The formulation according to claim 1, wherein the water-insoluble, film-forming polymer (c) is polyvinyl acetate.

5. The formulation according to claim 1, wherein the water-insoluble, film-forming polymer (c) is polyvinyl acetate in the form of an aqueous dispersion.

6. The formulation according to claim 1, wherein the water-soluble polymer (d) is polyvinylpyrrolidone.

7. The formulation according to claim 1, wherein the further pharmaceutically customary excipients (e) are acidifiers, sweeteners, flavors, flavor enhancers, colorants, thickeners, surfactants and finely divided pigments.

8. The formulation according to claim 1, wherein the excipient content A) composed of:
   a) 70-95% by weight of sugar or sugar alcohols,
   b) 2-15% by weight of the disintegrant,
   c) 1-10% by weight of water-insoluble, film-forming polymers,
   d) 0-10% by weight of water-soluble polyvinylpyrrolidone, and
   e) 0-15% by weight of further pharmaceutically customary excipients.

9. The formulation according to claim 1, wherein the excipient content A) composed of:

a) 75-95% by weight of mannitol or erythritol or a mixture thereof,
b) 3-10% by weight of the disintegrant,
c) 1-10% by weight of polyvinyl acetate,
d) 0-5% by weight of water-soluble polyvinylpyrrolidone, and
e) 0-15% by weight of further pharmaceutically customary excipients.

10. A tablet comprises a pharmaceutical formulation according to claim 1, wherein the tablet has a disintegration time of less than 60 seconds.

11. The tablet according to claim 10, wherein the tablet has a hardness between 40 N and 56 N.

12. The tablet according to claim 10, comprising from 20 to 99% by weight, based on the total tablet weight, of the pharmaceutical formulation.

13. A process for producing a pharmaceutical formulation according to claim 1, which comprises agglomerating:
A) an excipient content composed of:
   a) 60-97% by weight of sugar or sugar alcohols,
   b) 1-25% by weight of the disintegrant,
   c) 1-15% by weight of water-insoluble, film-forming polymers,
   d) 0-15% by weight of water-soluble polymers, and
   e) 0-15% by weight of further pharmaceutically customary excipients, the total of the components a) to e) being 100% by weight,
and
B) at least one pharmaceutically active ingredient,
in the presence of water.

14. The process according to claim 13, wherein the sugar or sugar alcohol a), disintegrant b) and pharmaceutically active ingredient B) are agglomerated with an aqueous dispersion of the water-insoluble polymer c).

15. The process according to claim 14, wherein the aqueous dispersion of the water-insoluble polymer further comprises suspended disintegrant.

16. The process according to claim 13, wherein the excipient content A) is agglomerated in a first step, and the resulting agglomerates are agglomerated with the pharmaceutically active ingredient B) in a second step.

17. The process according to claim 13, wherein the agglomeration takes place in a fluidized bed granulator, a mixer or a spray tower.

* * * * *